United States Patent [19]
Miwa et al.

[11] Patent Number: 6,042,544
[45] Date of Patent: Mar. 28, 2000

[54] NON-CONTACT TYPE TONOMETER

[75] Inventors: Tetsuyuki Miwa, Nukaga-gun; Munehiro Nakao, Toyokawa, both of Japan

[73] Assignee: Nidek Co., Ltd., Gamagori, Japan

[21] Appl. No.: 09/335,794

[22] Filed: Jun. 18, 1999

[30] Foreign Application Priority Data

Jul. 1, 1998 [JP] Japan .................. 10-186180

[51] Int. Cl.⁷ .................................................. A61B 3/016
[52] U.S. Cl. .......................................... 600/399; 600/405
[58] Field of Search .................................. 600/399, 401, 600/405; 514/522

[56] References Cited

U.S. PATENT DOCUMENTS

| | | | |
|---|---|---|---|
| 4,559,359 | 12/1985 | Matier | 514/522 |
| 4,621,644 | 11/1986 | Eilers | 600/405 |
| 4,951,670 | 8/1990 | Tamaka et al. | |
| 5,279,300 | 1/1994 | Miwa et al. | |
| 5,502,521 | 3/1996 | Katou | |
| 5,671,737 | 9/1997 | Harosi | 600/405 |

FOREIGN PATENT DOCUMENTS

| | | |
|---|---|---|
| B2-63-58577 | 11/1988 | Japan . |
| 63-300740 | 12/1988 | Japan . |
| 5-56931 | 3/1993 | Japan . |

*Primary Examiner*—George Manuel
*Attorney, Agent, or Firm*—Oliff & Berridge, PLC

[57] ABSTRACT

A non-contact type tonometer is disclosed, wherein a fluid blowing device blows a compressed air against a cornea of an examinee's eye, a deformation detection device detects a corneal deformed state caused by the fluid, a pressure detection device detects the fluid pressure to be blown by the fluid blowing device, a memory samples data on time-varying pressure detected by the pressure detection device at predetermined time intervals and stores them, and a calculation device takes a predetermined amount of pressure data from those stored in the memory, the pressure data being within a predetermined duration determined relative to the reference time at which a predetermined deformation of the cornea is detected by the deformation detection device. Then, the calculation device calculates an intraocular pressure of the examinee's eye based on the taken pressure data.

18 Claims, 4 Drawing Sheets

NON-CONTACT TYPE TONOMETER

BACKGROUND OF THE INVENTION

1. Field of the Invention

The present invention relates to a non-contact type tonometer for measuring intraocular pressure of an examinee's eye by blowing a compressed fluid against the cornea of the examinee's eye, and detecting a deformed state of the cornea.

2. Description of Related Art

There is conventionally known a non-contact type tonometer, as disclosed in Japanese Patent Publication No. SHO 63-58577, which measures intraocular pressure of an examinee's eye by blowing a compressed fluid such as air against the examinee's eye, thereby deforming the cornea of the examinee's eye, and directly obtaining a fluid pressure at the time the cornea is deformed into a flattened state from a pressure sensor disposed in a fluid pressure generator.

For an intraocular pressure calculation, however, the conventional tonometer is constructed to use a fluid pressure value at the time a predetermined corneal deformation of an examinee's eye is detected. Thus constructed tonometer has the following problems; for instance, when abnormal piston driving conditions are encountered in the fluid pressure generator, or errors such as a signal error of a pressure sensor caused by noises occur in a pressure detection system, thereby causing variations in pressure, the reliability of intraocular pressure measurement results is lowered.

SUMMARY OF THE INVENTION

The present invention has been made in view of the above circumstances and has an object to overcome the above problems and to provide a non-contact type tonometer capable of reducing the influence of a pressure variation even if it is occurred, and of providing measurement values with high reliability.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the purpose of the invention, there is provided a non-contact type tonometer for measuring intraocular pressure of an examinee's eye, the tonometer including fluid blowing means for blowing compressed fluid against a cornea of the examinee's eye, deformation detection means for detecting in time series a corneal deformed state caused by the fluid blown from the fluid blowing means, pressure detection means for detecting in time series pressure of the fluid to be blown from the fluid blowing means, sampling means for sampling, at predetermined time intervals, data on the pressure detected by the pressure detection means, memory means for storing the pressure data sampled by the sampling means, and calculation means which takes a predetermined amount of pressure data from the memory means and calculates the intraocular pressure based on the taken pressure data.

According to another embodiment of the present invention, there is provided a non-contact type tonometer for measuring intraocular pressure of an examinee's eye, the tonometer including an air blowing device, provided with a cylinder and a piston disposed in the cylinder, which blows air compressed by actuation of the piston against a cornea of the examinee's eye, a deformation detection optical system which detects in time series a deformed state of the cornea deformed by the blown air, a pressure sensor which detects in time series an air pressure in the cylinder, a controller which samples, at predetermined time intervals, data on the pressure detected by the pressure sensor, and a memory in which the pressure data sampled by the controller is stored, wherein the controller takes a predetermined amount of pressure data from the memory and calculates the intraocular pressure based on the taken pressure data.

The above constructed non-contact type tonometer of the present invention can provide measurement values with stability and high reliability, and unaffected by pressure variations caused by noises and the like in the pressure detection means which detects the pressure of a compressed air.

BRIEF DESCRIPTION OF THE DRAWINGS

The accompanying drawings, which are incorporated in and constitute a part of this specification illustrate an embodiment of the invention and, together with the description, serve to explain the objects, advantages and principles of the invention.

In the drawings,

FIG. 3(*b*) is a diagram showing a sampling example of data on the pressure signal Pn and the pressure applanation signal Qn, taken from the data shown in FIG. 3(*a*)

DETAILED DESCRIPTION OF THE PREFERRED EMBODIMENTS

Figure 1:
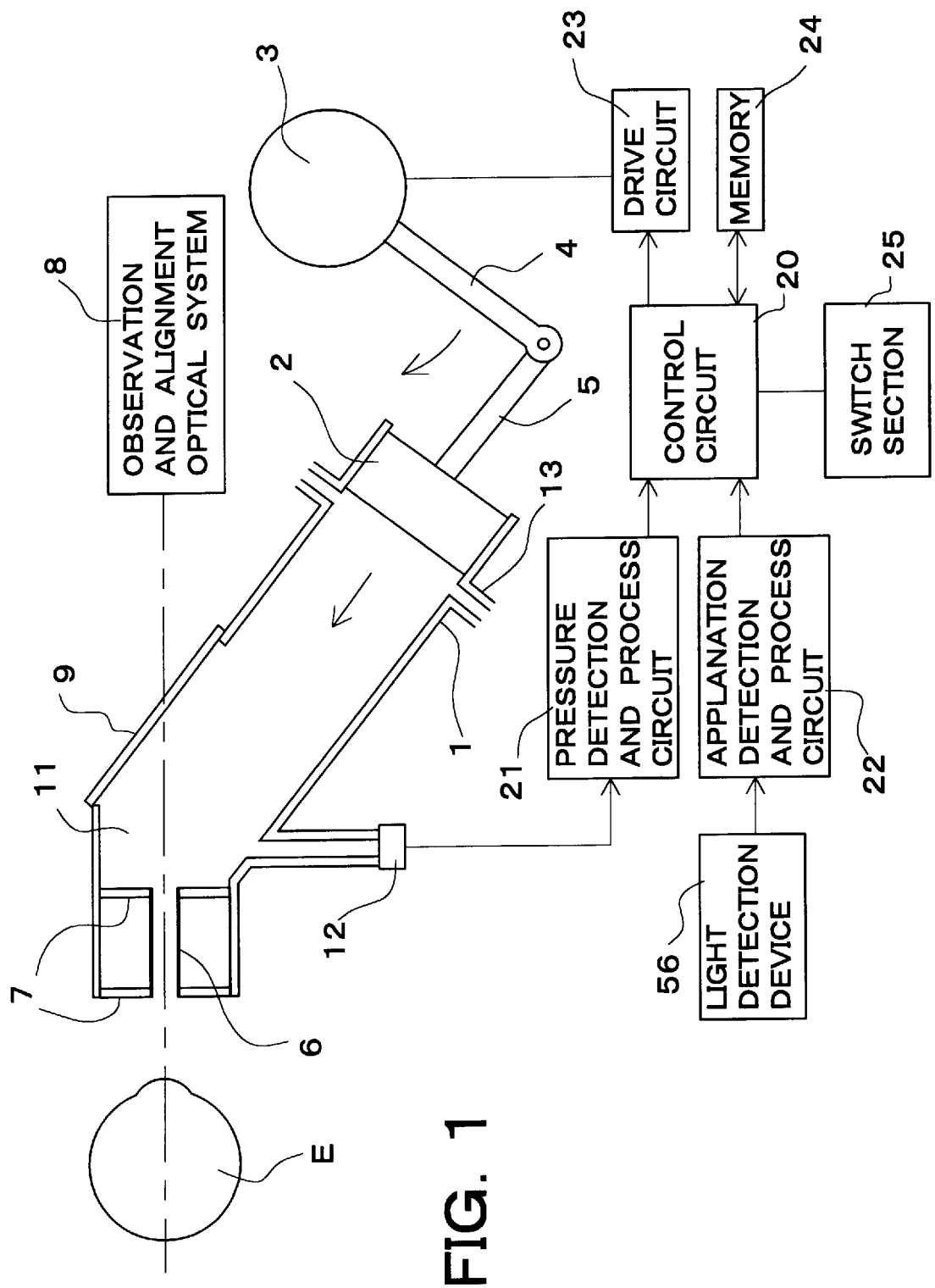
FIG. 1 is a view showing a schematic side structure of a fluid blowing mechanism and a control system for a non-contact type tonometer in an embodiment according to the present invention.
Figure 2:
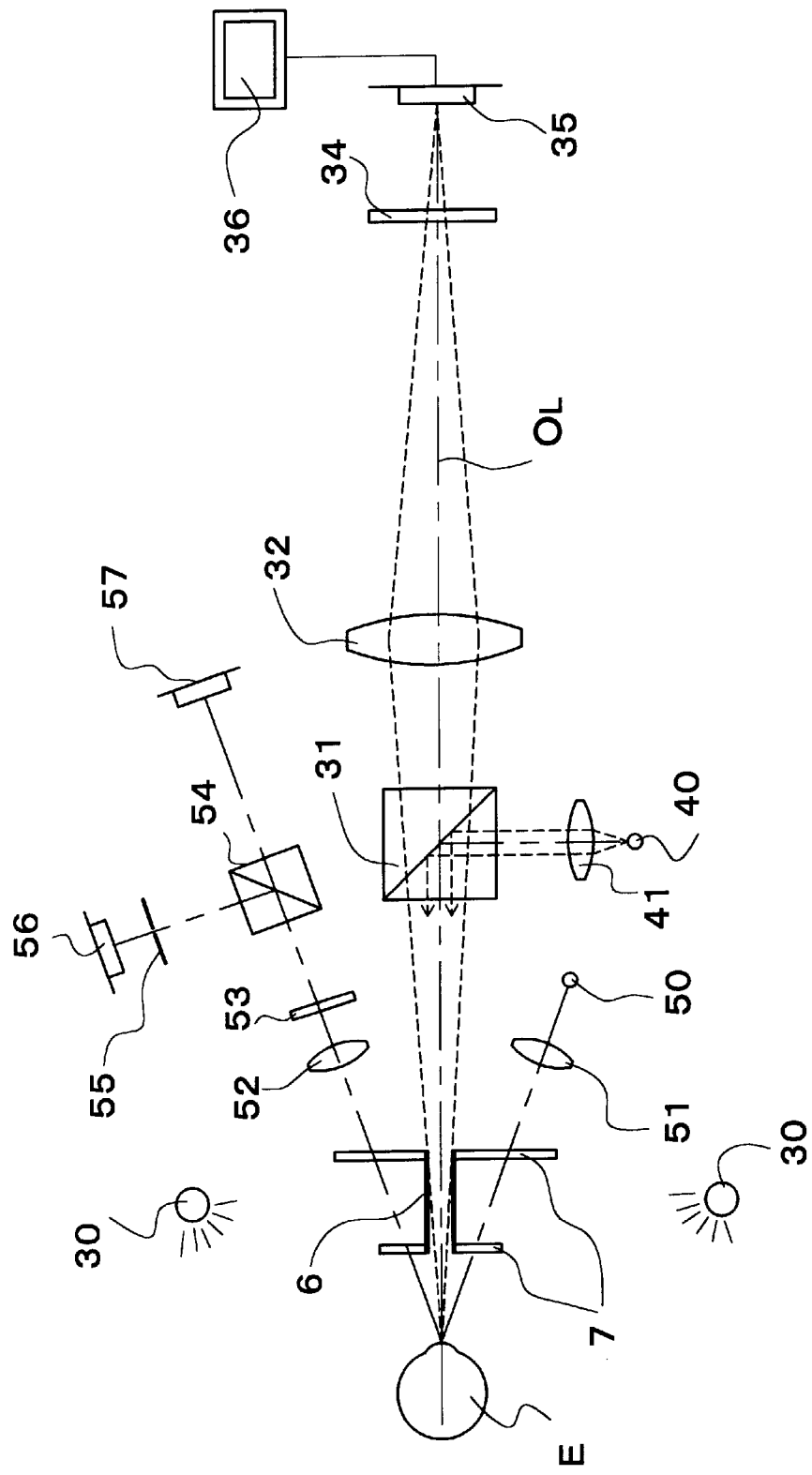
FIG. 2 is a schematic view showing an optical system of the non-contact type tonometer in the embodiment.

A detailed description of a preferred embodiment of a non-contact type tonometer embodying the present invention will now be given referring to the accompanying drawings. FIG. 1 is a view showing a schematic side structure of a fluid blowing mechanism and a control system for a non-contact type tonometer in the present embodiment; and FIG. 2 is a schematic view showing an optical system of the non-contact type tonometer.

[Fluid blowing mechanism]

In a cylinder 1, as a piston 2 is moved up by actuation of a solenoid 3, the air is compressed into an air compression chamber 11, thus generating fluid pressure. The compressed air is blown through a nozzle 6 against a cornea of an examinee's eye E.

Reference numeral 7 indicates a transparent glass plate which holds the nozzle 6 and transmits observation light or alignment light of an optical system which will be mentioned later. The glass plate 7 also constitutes a side wall of the air compression chamber 11. Reference numeral 9 indicates a transparent glass plate disposed behind the nozzle 6 and constitutes a rear wall of the air compression chamber 11. The glass plate 9 transmits observation light or alignment light. Behind the glass plate 9 is arranged an observation and alignment optical system which will be mentioned later.

Numeral 12 indicates a pressure sensor for detecting the pressure in the air compression chamber 11.

[Optical system]

In FIG. 2, an image of the examinee's eye E illuminated by the infrared rays emitted from infrared light sources 30 is formed on a CCD camera 35 through a beam splitter 31, an objective lens 32, and a filter 34. This filter 34 has the property of passing the light of the light source 30 and that of an alignment light source 40, while not passing the light of a light source 50 for corneal deformation detection which will be mentioned later. The image thus formed on the CDD camera 35 is displayed on a monitor 36. A dash-single-dot line $O_L$ indicates an optical axis of this observation optical system, and agrees with a central axis of the nozzle 6.

Reference number 40 indicates an infrared LED which is a light source for alignment. An infrared light emitted from the light source 40 and projected through a projection lens 41 is reflected by the beam splitter 31, and focused on the examinee's eye E from a front side thereof. A luminescent spot is then formed on the cornea of the examinee's eye E by the light from the light source 40 and is focused on the CCD camera 35 through the beam splitter 31, the objective lens 32, and the filter 34. This luminescent spot is used for alignment of the non-contact type tonometer with respect to the examinee's eye E.

Reference numeral 50 indicates an LED which is a light source for corneal deformation detection. The light emitted from the light source 50 is made into substantial parallel luminous flux by a collimator lens 51, and is projected onto the cornea of the eye E. The light reflected by the cornea passes through a light-receiving lens 52 and a filter 53 having the property of not passing the light of the light sources 30 and 40, and the light is reflected by a beam splitter 54. Then, the reflected light passes through a pinhole plate 55 and is received by a light detection device 56. This optical system for corneal deformation detection is arranged so that the light quantity in the light detection device 56 becomes maximum when the cornea of the examinee's eye E is deformed into a flattened state.

A part of this corneal deformation detection optical system is used in common for a working distance detection optical system. The light having passed the beam splitter 54 is incident on a one-dimensional detecting element 57. A working distance is detected on the basis of the output signal from the detecting element 57.

[Control system]

In FIG. 1, reference numeral 20 indicates a control circuit for controlling the whole apparatus. An output signal of the pressure sensor 12 and an output signal of the light detection device 56 are input into the control circuit 20 through a pressure detection and process circuit 21 and an applanation detection and process circuit 22, respectively. The control circuit 20 conducts a predetermined calculation processing based on each of the output signals input into the control circuit 20 to determine the intraocular pressure of the examinee's eye E. Reference numeral 23 indicates a driving circuit for driving the solenoid 3. Reference numeral 24 indicates a memory which stores data on time-varing pressure detected in the pressure sensor 12, and other information. Reference numeral 25 indicates a switch section including a switch for switching a measurement range of the pressure of the fluid to be blown through the nozzle 6 when the pressure is measured. The measurement range may be selected from two kinds; 30 mmHg and 60 mmHg. The rising time and the upper limit of the fluid pressure to be blown are changed as the driving speed of the solenoid 3 is changed.

The following explanation puts emphasis on the intraocular pressure calculating operation in the non-contact type tonometer constructed as above.

While observing the image of an anterior part of the examinee's eye E and the luminescent spot for alignment displayed on the monitor 36, an examiner performs alignment in up-and-down and right-and-left directions. Since the working distance direction is displayed as a guide index on the monitor 36 based on the positional information obtained from the detection element 57, the examiner performs alignment adjustment for the working distance direction in accordance with the guide index.

After the alignment in each direction as mentioned above, when the examiner presses a measurement start switch not illustrated (or the control circuit 20 automatically sends a measurement start signal in accordance with a detection signal from the alignment optical system), the control circuit 20 causes the driving circuit 23 to actuate the solenoid 3. The piston 2 raised by the actuation of the solenoid 3 compresses the air in the cylinder 1 to blow the compressed air through the nozzle 6 against the cornea of the examinee's eye E. Thus, the cornea is gradually deformed by a blow of the compressed air. When the cornea is made into a flattened state, the light emitted from the light source 50 and reflected by the cornea is incident at the maximum light quantity on the light detection device 56. The output signals of the pressure sensor 12 and the light detection device 56 are sequentially processed in the process circuits 21 and 22 respectively and input into the control circuit 20.

Figure 3:
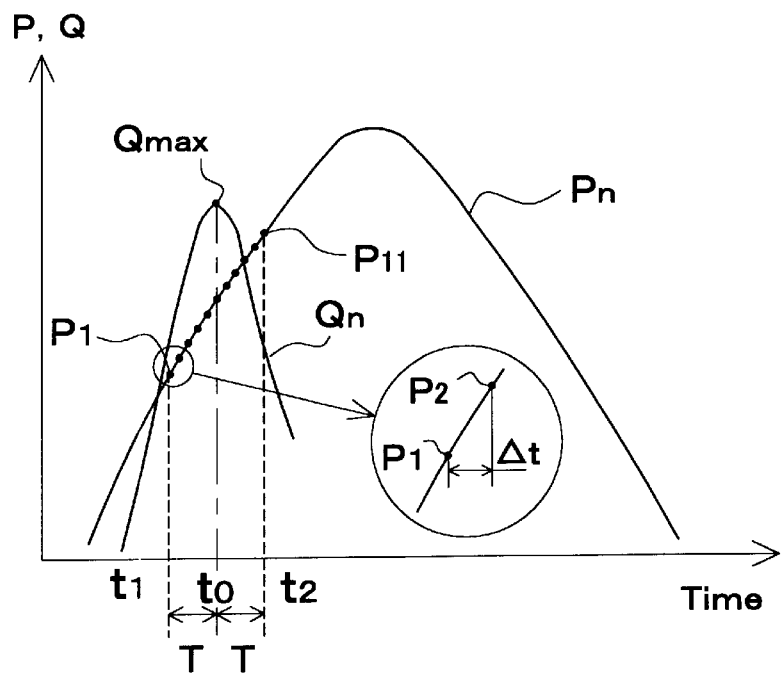
FIG. 3(*a*) is a diagram showing time-series changes of a pressure signal Pn and an applanation signal Qn.
Figure 3:
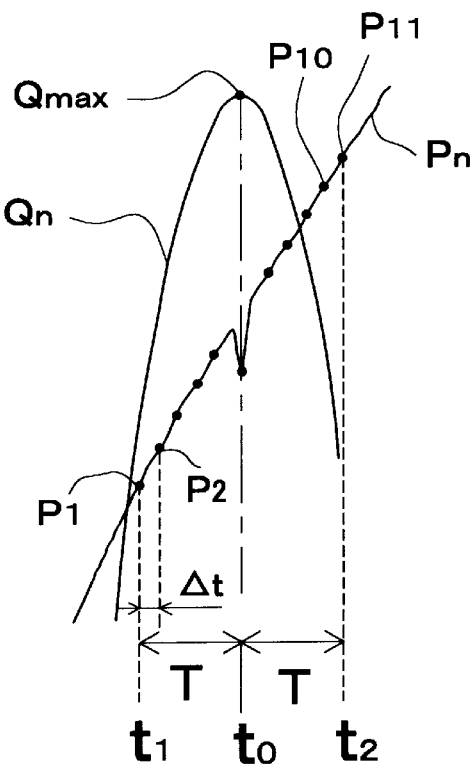
Figure 4:
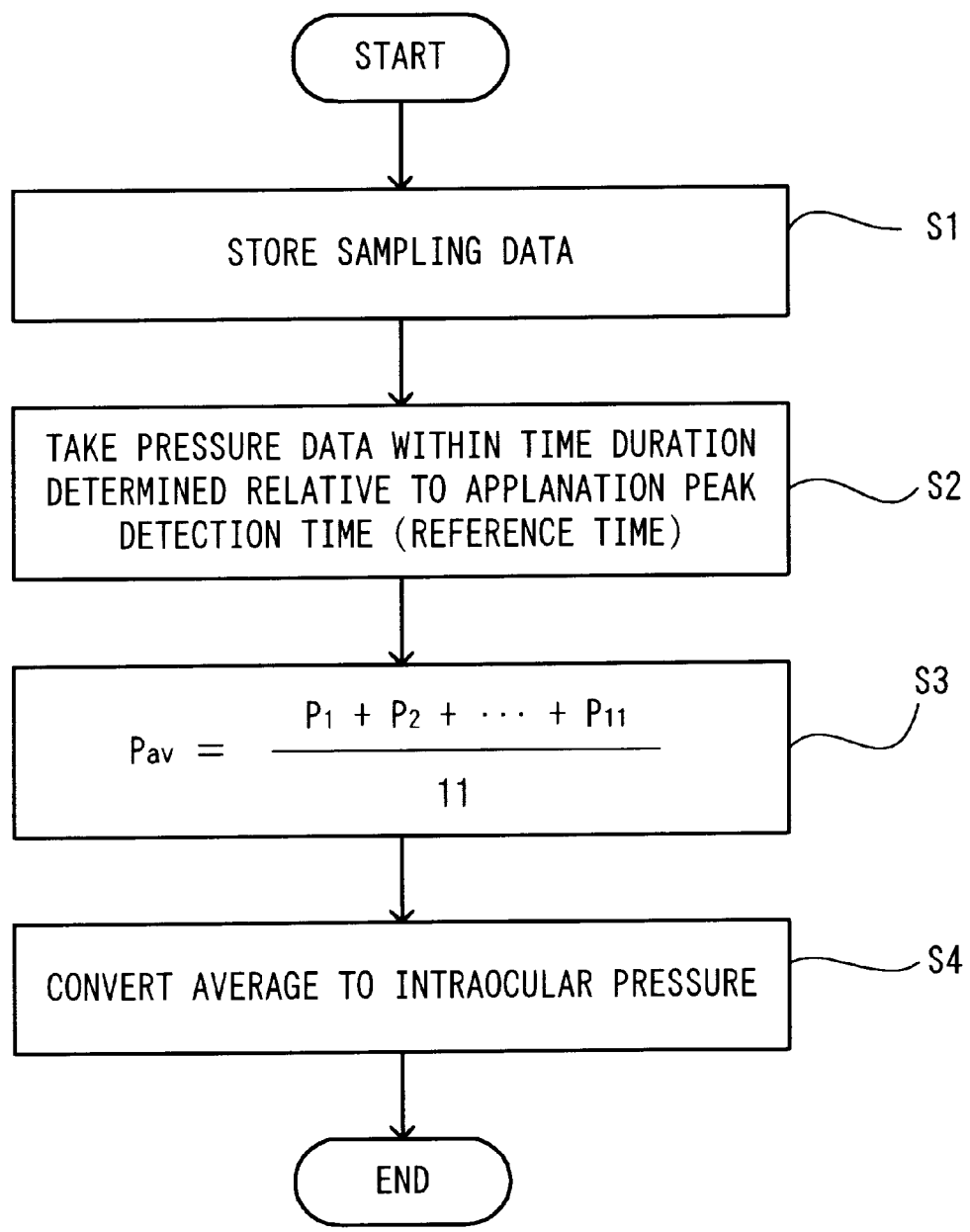
FIG. 4 is a flow chart showing steps for processing an intraocular pressure calculation.

FIG. 3(a) is a diagram showing time-series changes of a pressure signal $P_n$ obtained from the output signal of the pressure sensor 12 and an applanation signal $Q_n$ obtained by the output signal from the light detection device 56. FIG. 4 is a flow chart of showing steps for processing an intraocular pressure calculation.

The control circuit 20 samples data on the pressure signal $P_n$ and the applanation signal $Q_n$ at predetermined time intervals $\Delta t$ from the start of blowing the compressed air against the cornea by the actuation of the solenoid 3 to the completion of the blow (i.e., from a pressure detection start time till a predetermined time has elapsed), and stores the sampled data in the memory 24 together with the detection times (S1). When the blow of the compressed air is completed, the control circuit 20 takes, relative to the reference time $t_0$ at which the maximum value $Q_{max}$ of the sampled data on the applanation signal $Q_n$ is obtained, data on pressure values between the first time $t_1$ and the second time $t_2$ which are determined to have a predetermined time duration T before and after the reference time $t_0$, respectively, (by reading the pressure values from the memory 24) (S2).

For instance, assuming the data sampling time interval $\Delta t$ of the pressure signal $P_n$ and the applanation signal $Q_n$ to be 0.1 msec and the duration T to be 0.5 msec, the total duration between the first and second times $t_1$ and $t_2$ is 1.0 msec, in which eleven data on the pressure values $P_1$ to $P_{11}$ are taken (see FIG. 3(b)). At this time, the pressure value at the reference time $t_0$ which is in the middle between the first and second times $t_1$ and $t_2$ may be eliminated, because it will occur a case that the pressure value corresponding to the reference time $t_0$ is not reliable due to the abnormality in the pressure sensor 12, as shown in FIG. 3(b).

Next, the taken pressure values P1 to P11 are averaged by the following expression to provide the average $P_{av.}$ (S3):

$$P_{av.} = (P_1 + P_2 + \ldots + P_{11})/11$$

This can also be expressed in a general expression:

$$P_{av.}=(P_1+P_2+\ldots+P_n)/n$$

wherein "n" indicates the number of sampled pressure values.

Thus obtained pressure average is converted to intraocular pressure. The measurement result is thus obtained (S4).

In this way, by averaging the pressure data within the duration between the first and second times $t_1$ and $t_2$, placing the reference time $t_0$ in the middle therebetween, more stable and high reliable result can be obtained even when variations or partial errors caused by noise or the like occur in the pressure signal $P_n$ of the pressure sensor 12, for example, as shown in FIG. 3(b), as compared with the case of using the as-is pressure value data at the reference time $t_0$ at which the maximum value $Q_{max}$ which is a peak of the applanation signal $Q_n$ is obtained.

It is to be noted that, to obtain the above average $P_{av.}$, the sampling data to be taken may be determined by the number of sampling data (which is set to be equal in number after and before the reference time $t_0$), instead of the duration mentioned above.

The time interval $\Delta t$ of the sampling data may be changed according to the inclination (a changing ratio to time) of the applanation signal $Q_n$ to be detected or the inclination of the pressure signal $P_n$ to be detected. For instance, in case of the examinee's eye which may provide a sharp inclination of the applanation signal $Q_n$, the detection accuracy of a peak of the applanation signal $Q_n$ is deteriorated if the time interval $\Delta t$ of the sampling data is long. In this case, it is requested to shorten the time interval $\Delta t$ by checking the variation at the rising of the applanation signal $Q_n$, so that the peak time of the applanation signal $Q_n$ can be obtained with more accuracy.

In case of a large inclination of the pressure signal $P_n$ (and in case of switching the pressure of the measurement range from 30 mmHg to 60 mmHg), the pressure changing ratio to time increases, and therefore the detection accuracy of a peak of the applanation signal $Q_n$ exerts an influence on the accuracy of an intraocular pressure calculation. Thus, similarly in this case, when the time interval $\Delta t$ is shortened to obtain sampling data at close intervals, the pressure value at about the peak of the applanation signal $Q_n$ can be precisely reflected in the intraocular pressure calculation.

It is to be noted that, if the time interval $\Delta t$ is shortened as above, the predetermined number of data to be stored in the memory 24 can be early obtained, though the unnecessary data for the intraocular pressure calculation may be deleted and the time interval $\Delta t$ may be lengthened in the part except the necessary part for the intraocular pressure calculation.

As mentioned above in detail, the non-contact type tonometer in the embodiment can provide measurement values with stability and high reliability, and unaffected by pressure variations caused by noises and the like in the pressure detection system which detect the pressure of a compressed air.

The foregoing description of the preferred embodiment of the invention has been presented for purposes of illustration and description. It is not intended to be exhaustive or to limit the invention to the precise form disclosed, and modifications and variations are possible in light of the above teachings or may be acquired from practice of the invention. The embodiment chosen and described in order to explain the principles of the invention and its practical application to enable one skilled in the art to utilize the invention in various embodiments and with various modifications as are suited to the particular use contemplated.

It is intended that the scope of the invention be defined by the claims appended hereto, and their equivalents.

What is claimed is:

1. A non-contact type tonometer for measuring intraocular pressure of an examinee's eye, the tonometer including:
   fluid blowing means for blowing compressed fluid against a cornea of the examinee's eye;
   deformation detection means for detecting in time series a corneal deformed state caused by the fluid blown from the fluid blowing means;
   pressure detection means for detecting in time series pressure of the fluid to be blown from the fluid blowing means;
   sampling means for sampling, at predetermined time intervals, data on the pressure detected by the pressure detection means;
   memory means for storing the pressure data sampled by the sampling means; and
   calculation means which takes a predetermined amount of pressure data from the memory means and calculates the intraocular pressure based on the taken pressure data.

2. The non-contact type tonometer according to claim 1, wherein the calculation means calculates the intraocular pressure based on an averaged value of the taken pressure data.

3. The non-contact type tonometer according to claim 1, wherein the calculation means takes the predetermined amount of pressure data, relative to a reference time at which a predetermined deformation state is detected by the deformation detection means.

4. The non-contact type tonometer according to claim 3, wherein the calculation means takes, relative to the reference time at which the predetermined deformation state is detected, the predetermined amount of pressure data between a first time and a second time which are set with a same duration before and after the reference time.

5. The non-contact type tonometer according to claim 3, wherein the calculation means takes, relative to the reference time at which the predetermined deformation state is detected, the predetermined amount of pressure data which are set in a same number before and after the reference time.

6. The non-contact type tonometer according to claim 1, wherein the sampling means samples, at predetermined intervals, data on the corneal deformed state detected by the deformation detection means, together with the pressure data.

7. The non-contact type tonometer according to claim 6, further including time interval changing means for changing a time interval of sampling to be performed by the sampling means.

8. The non-contact type tonometer according to claim 7, wherein the time interval changing means changes the time interval of sampling based on a degree of a corneal deformed state detected in time series by the deformation detection means.

9. The non-contact type tonometer according to claim 1, further including time interval changing means for changing a time interval of sampling to be performed by the sampling means.

10. The non-contact type tonometer according to claim 9, further including fluid pressure changing means for changing a changing ratio of pressure-to-time of the fluid to be blown by the fluid blowing means,
    wherein the time interval changing means changes the time interval of sampling based on the fluid pressure changed by the fluid pressure changing means.

11. A non-contact type tonometer for measuring intraocular pressure of an examinee's eye, the tonometer including:

an air blowing device, provided with a cylinder and a piston disposed in the cylinder, which blows air compressed by actuation of the piston against a cornea of the examinee's eye;

a deformation detection optical system which detects in time series a deformed state of the cornea deformed by the blown air;

a pressure sensor which detects in time series an air pressure in the cylinder;

a controller which samples, at predetermined time intervals, data on the pressure detected by the pressure sensor; and a memory in which the pressure data sampled by the controller is stored, wherein the controller takes a predetermined amount of pressure data from the memory and calculates the intraocular pressure based on the taken pressure data.

12. The non-contact type tonometer according to claim 11, wherein the controller calculates the intraocular pressure based on an averaged value of the taken pressure data.

13. The non-contact type tonometer according to claim 11, wherein the controller takes the predetermined amount of pressure data, relative to a reference time at which a predetermined deformation state is detected by the deformation detection optical system.

14. The non-contact type tonometer according to claim 13, wherein the controller takes, relative to the reference time at which the predetermined deformation state is detected, the predetermined amount of pressure data between a first time and a second time which are set with a same duration before and after the reference time.

15. The non-contact type tonometer according to claim 13, wherein the controller takes, relative to the reference time at which the predetermined deformation state is detected, the predetermined amount of pressure data which are set in a same number before and after the reference time.

16. The non-contact type tonometer according to claim 11, wherein the controller samples, at predetermined intervals, data on the corneal deformed state detected by the deformation detection optical system, together with the pressure data.

17. The non-contact type tonometer according to claim 16, wherein the time interval of sampling to be performed by the controller is changeable based on a degree of a corneal deformed state detected in time series by the deformation detection optical system.

18. The non-contact type tonometer according to claim 11, further including a fluid pressure changing device which changes a changing ratio of pressure-to-time of the air to be blown by the air blowing device, wherein the time interval of sampling to be performed by the controller is changeable based on the air pressure which is changed by the fluid pressure changing device.

* * * * *